United States Patent
Morris et al.

(10) Patent No.: US 6,939,708 B2
(45) Date of Patent: *Sep. 6, 2005

(54) METHOD OF RAPID BIO-CYCLING OF AN AQUARIUM

(75) Inventors: Barrington A. Morris, Coral Springs, FL (US); Eric A. Goulbourne, Jr., Hamilton, OH (US)

(73) Assignee: World Wide Imports Enterprises, Inc., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/978,947

(22) Filed: Oct. 16, 2001

(65) Prior Publication Data

US 2002/0039782 A1 Apr. 4, 2002

Related U.S. Application Data

(63) Continuation of application No. 09/438,672, filed on Nov. 12, 1999, now Pat. No. 6,376,229.
(60) Provisional application No. 60/117,959, filed on Jan. 29, 1999.

(51) Int. Cl.[7] .......................... C12N 1/04; A01K 63/04; A01K 63/00
(52) U.S. Cl. ...................... 435/262; 435/260; 119/245; 119/260
(58) Field of Search ............................... 435/262, 260; 119/245, 260

(56) References Cited

U.S. PATENT DOCUMENTS

| | | | |
|---|---|---|---|
| 4,392,892 A | * | 7/1983 | Wagner et al. |
| 4,874,707 A | | 10/1989 | Bock |
| 4,995,980 A | * | 2/1991 | Jaubert |
| 4,999,301 A | | 3/1991 | Bryan-Jones |
| 5,314,542 A | | 5/1994 | Cassidy |
| 5,733,774 A | | 3/1998 | Jin |
| 6,376,229 B2 | * | 4/2002 | Morris et al. |

OTHER PUBLICATIONS

Kawai et al. Memoirs of the Research Institute for Food Science, Kyoto University (1971), No. 32, pp. 7–15.*
Melin et al. International Biodeterioration and Biodegradation. (1996) pp. 9–18.*
Kerry et al. Aquaculture 1996, 144: 103–119.*

* cited by examiner

Primary Examiner—Vera Afremova
(74) Attorney, Agent, or Firm—Mark D. Bowen, Esq.; Stearns Weaver Miller Weissler Alhadeff & Sitterson, P.A.

(57) ABSTRACT

A method of rapid biochemical cycling of aquariums using naturally preserved granular marine substrate material, such as sand or aragonite, to rapidly denitrify the aquatic environment and to establish biochemical conditions that are favorable to the survival and viability of fish, crustaceans, invertebrates, and other marine aquatic life. The method includes the steps of harvesting and packaging marine sand such that marine microorganisms, in the form of biofilm attached to the sand, are preserved with an optimal amount of water and air in retail packaging specifically dimensioned and configured for maintaining ammonia oxidizing bacteria in a state wherein the bacteria are capable of metabolic and physiologic activity after prolonged periods at room temperature. Harvesting and packaging marine microorganisms according to the disclosed method allows for widespread distribution to consumers through conventional retail sales channels. Rapid biochemical cycling of an aquarium is achieved by introducing the contents of the packaging into an aquarium whereby marine microorganism biofilm instantly contributes to establishing a healthy aquatic environment by reducing harmful ammonia levels and through denitrification.

15 Claims, 3 Drawing Sheets

Figure 1

Sea Water Enrichment Solution

To 940 mL of sea water add:

| Quantity | Compound | Stock Solution |
|---|---|---|
| 1.0 mL | $NaNO_3$ | 75.0 g/L of distilled water |
| 1.0 mL | $NaH_2PO_4 \cdot H_2O$ | 5.0 g/L of distilled water |
| 1.0 mL | Trace Metal Solution | (see Figure 2) |
| 0.5 mL | Vitamin Solution | (see Figure 3) |
| 50 mL | Organics Stock Solution | (see Figure 4) |

Make final volume up to 1.0 L with sea water. Filter sterilize after all additions.

Figure 2

Trace Metal Solution

To 950 mL of distilled water add:

| Quantity | Compound | Stock Solution |
|---|---|---|
| 3.15 g | $FeCl_3 \cdot 6H_2O$ | - |
| 4.36 g | $Na_2EDTA \cdot 2H_2O$ | - |
| 1.0 mL | $SrCl_2 \cdot 6H_2O$ | 9.8 g/L distilled water |
| 1.0 mL | $K_2MoO_4 \cdot 2H_2O$ | 6.3 g/L distilled water |
| 1.0 mL | $ZnSO_4 \cdot 7H_2O$ | 22.0 g/L distilled water |
| 1.0 mL | $CoCl_2 \cdot 6H_2O$ | 10.0 g/L distilled water |
| 1.0 mL | $MnCl_2 \cdot 4H_2O$ | 180.0 g/L distilled water |

Make final volume up to 1.0 L with distilled water. Filter sterilize.

Figure 3

Vitamin Solution

To 950 mL distilled water add:

| Quantity | Compound | Stock Solution |
| --- | --- | --- |
| 1.0 mL | Vitamin B12 (Cyanocobalamin) | 1.0 g/L of distilled water |
| 10.0 mL | Biotin | 0.1 g/L of distilled water |
| 200.0 mg | Thiamine HCl | - |

Make final volume up to 1.0 L with distilled water. Filter sterilize into plastic vials and store in refrigerator.

Figure 4

Organics Stock Solution

To 900 mL of distilled water add:

| Quantity | Compound |
| --- | --- |
| 1.0 g | Sodium Acetate |
| 6.0 g | Glucose |
| 3.0 g | Sodium Succinate |
| 4.0 g | Peptone |
| 2.0 g | Yeast extract |

Bring up to 1.0 L with distilled water. Filter sterilize and dispense into 50 mL aliquots.

Viable Bacteria Per Pound of Argonite

METHOD OF RAPID BIO-CYCLING OF AN AQUARIUM

CROSS-REFERENCE TO RELATED APPLICATIONS

This application is a continuation of U.S. patent application Ser. No. 09/438,672, filed Nov. 12, 1999 now U.S. Pat. No. 6,376,229, which claims the benefit of U.S. Provisional Patent Application Ser. No. 60/117,959, filed Jan. 29, 1999, each of which are incorporated herein by reference.

STATEMENT REGARDING FEDERALLY SPONSORED RESEARCH OR DEVELOPMENT

Not Applicable

BACKGROUND OF THE INVENTION

1. Field of the Invention

The present invention relates to the initial biochemical cycling of marine aquariums, and, more particularly to a method of rapid biochemical cycling of aquariums using naturally preserved granular marine substrate material, such as sand or aragonite, to rapidly denitrify the aquatic environment and to establish biochemical conditions that are favorable to the survival and viability of fish, crustaceans, invertebrates, and other marine aquatic life.

2. Description of Related Art

Aquariums have experienced a boom in popularity in recent years. Many saltwater aquariums include a diverse mix of tropical fish, live coral formations, and other exotic marine life. Saltwater marine organisms are directly affected by the chemical, biological, and physical characteristics of their environment. A number of environmental factors are critical to maintaining the delicate balance required for a healthy aquarium environment. Factors such as water temperature, pH level, lighting conditions, and complex chemical balances must constantly be maintained and monitored. The introduction of fish and other marine animals into an aquarium causes a series of chemical changes often resulting in chemical imbalances that are not conducive to aquatic life. It is therefore crucial to maintain a high level of water quality.

The initial set up of a marine aquarium typically requires a conditioning period that can take up to six (6) weeks depending upon the aquarium conditions and temperature. During the conditioning period the chemical composition of the water undergoes a series of changes and waste products can quickly build-up to levels that are toxic to aquarium life. The introduction of fish, plants, and food into an aquarium begins a natural process often referred to a "biochemical cycling".

A significant change in the chemical composition of the water involves the accumulation of ammonia. The process begins when fish and invertebrates excrete waste. The excreted waste increases the amount of ammonia present in the water as a result of decaying food and organic compounds. Harmful ammonia and nitrite are constantly converted into less harmful nitrates, which in turn is used by plants and algae for food. Aquariums are full of both autotrophic and heterotrophic bacteria that attach, grow, and form biofilms where the bacteria convert toxic nitrogenous compounds and ammonia into harmless products. *Nitrobacter* and *Nitrosomonas* are examples of autotrophic bacteria that use oxygen to oxidize ammonia ($NH_4$) to nitrite ($NO_2$) and Nitrate ($NO_3$).

Ammonia is a toxic waste product which, if unchecked, can accumulate and cause injury or death to aquarium inhabitants. In fact, the presence of ammonia in aquarium water is the main cause of death in aquarium fish. The primary sources of ammonia are decaying organic material (such as uneaten food) and waste excreted by fish, other animals and organisms. An ammonia level as low as 0.5 parts-per- million (PPM) creates stress in fish and compromises the natural immune systems of fish and other aquarium inhabitants. An ammonia level of 2 PPM has been found to cause the natural immune system of the fish and other aquarium inhabitants to fail or otherwise cease functioning. Accordingly, maintaining ammonia levels is critical to the health of the aquarium habitat.

The accumulation of ammonia is often caused by the lack of sufficient numbers of *Nitrosomonas*. *Nitrosomonas* is a genus of bacteria in aquaria that oxidize ammonia thereby regulating the ammonia level. *Nitrosomonas*, and other ammonia oxidizing bacteria, are found in natural abundance in marine materials, such as sand, aragonite, and crushed coral, harvested from the ocean floor. Nature provides many types of bacteria that, in the presence of oxygen, carry out the oxidation of ammonia to nitrites and eventually to nitrates in a process known as nitrification. It has been found that such bacteria settle on marine materials, such as aragonite (reef sand), and eventually form a biofilm. Marine nitrifying bacteria in the biofilm oxidize ammonia to nitrite, and nitrite to nitrate. Accordingly, these natural marine materials provide a natural source of ammonia oxidizing bacteria for use in maintaining ammonia levels in aquarium environments. Nitrate not utilized by plants is removed by other bacteria in the absence of oxygen (the anaerobic environment found in the lower levels of the sediment) in a process called denitrification.

While marine nitrifying bacteria are found in abundance in natural materials, such as aragonite harvested from the ocean floor, it has been found that there are generally three conditions that are required to maintain the nitrification process. These conditions are: (1) a surface upon which bacteria can attach, grow, and form a biofilm; (2) ammonia to start the process; and (3) an aerobic environment. The absence of any of the above-referenced conditions will either prevent or delay the nitrification process.

The initial set-up of aquariums presents unique biochemical circumstances that must be addressed in order to produce and maintain a healthy environment for marine life. The initial cycling of organic compounds in an aquarium started with dry sand or gravel often takes a period of several weeks during which an ammonia source (often only one or two small fish) provides an environment wherein beneficial bacteria to establish and begin to flourish eventually forming a biofilm. It has been found that the long initial cycling period realized when starting an aquarium with dry sand or gravel results from the time required for bacteria to attach, grow and form a biofilm on the previously dry, and organically inactive, sand and gravel. It has been shown that the initial cycling period can be substantially reduced by the introduction of bacteria rich "wet" sand and gravel that has been recently harvested from the ocean and thus contains an abundance of bacterial biofilm. Marine sand and gravel harvested from the ocean or riverbeds contain both autotrophic and heterotrophic bacteria in their natural state (i.e. established biofilms on the sand particles), each of which facilitate the rapid cycling of an aquarium. Accordingly, there exists a need for a method of harvesting and packaging marine materials such as aragonite reef sand, gravel, crushed coral and the like, such that the bacteria remain metabolically and physiologically active for extended periods of time in excess of twelve (12) months in retail packaging at room temperature. There further exists a need for a method of introducing a harvested and packaged natural granular marine substrate material into an aquarium such that the biochemical cycling process performs rapidly, and the aquatic life is stabilized and maintained naturally.

It has proven difficult, however, to maintain ammonia oxidizing bacteria and other useful bacteria in a biologically active state during the extended period beginning with the harvesting of the material and ending with the purchase by a consumer and delivery into an aquarium; a time period often reaching up to six (6) months or more. The difficulty is increased where the harvested materials must be stored for extended periods in retail packaging at room temperatures. It has also proven difficult to provide a rapid biochemical cycling method containing an abundance of marine bacterial biofilm that closely resembles the natural ocean process in a miniature ecosystem such as an aquarium.

The background art reveals several references directed to preserving bacteria and the like, but none of the references adequately address the problems encountered in maintaining ammonia oxidizing bacteria in a bio-actively viable bio-film for extended periods. The background art also reveals several references directed to the biochemical cycling process involving artificial and external filtration methods, however, none adequately address the problems encountered when attempting to easily and effectively introduce natural granular substrate material into an aquarium, whereby rapid bio-cycling occurs, promoting a healthy and stable environment for aquatic life.

U.S. Pat. No. 4,874,707, issued to Bock, discloses a complex laboratory process for producing an aqueous suspension of nitrifying bacteria using a growth medium containing ammonia or nitrite, in which the bacteria remain metabolically and physiologically active even after a storage period of one year or more at 30° C. (i.e. approximately room temperature). According to Bock, air, pure oxygen, or a mixture of air and pure oxygen is passed through a gas permeable non-porous tube submerged in a suitable culture medium. As a result of positive aerotaxis, nitrifying bacteria adhere on the tube surface, forming a biofilm of extracellular polymers. The bacteria are grown in the dark at a constant temperature of 30° C. When a stationary growth phase has been reached the oxygen supply is stopped.

U.S. Pat. No. 4,999,301, issued to Bryan-Jones, a method whereby microorganisms are stored for long periods of time in storage mediums containing a high concentration of nutrients and growth inhibiting substances to maintain the microorganisms, such as bacteria, in the stationary phase of their growth cycle. The concentrated medium disclosed by Bryan-Jones contains an excess of essential nutrients while the microorganisms are in the "death phase." When the concentrated medium is diluted to below the concentration that inhibits microorganism growth, the microorganisms will start to increase in number and grow. The claims of the Bryan-Jones reference are limited to bacteria selected from the group comprising *Lactobacillus plantarum* and *Bacillus subtilus*. E.g. claim 1. In addition, the '301 patent claims a bacterial culture kit having bacteria in a growth medium comprising from 10% to about 30% solids which function to delay the onset of the normal "death phase". The solids are disclosed as waste products from a food manufacturing process or an alcohol fermentation process. See, e.g. Column 2, lines 46–58. Bryan-Jones discloses a storage medium consisting of wheat spent wash syrup and acetate/acetic acid buffer and sucrose. Bryan-Jones claims that an advantage of such a kit is that a sufficient number of the microorganisms will remain viable when the kit is sold to a consumer such that the microorganisms will start to increase in number and grow after purchase.

U.S. Pat. No. 5,314,542, issued to Cassidy et al., discloses a culture of *Nitrosomonas* packaged in a manner to induce a metabolic state of dormancy under conditions favorable for survival of up to at least one year at room temperature. Upon obtaining culturing media with the maximum obtainable cell concentration, the media is concentrated to approximately one twenty-fifth ($1/25$) of its volume by centrifugation or filtration. See Col. 3, lines 5–9. The concentrate is re-suspended in sterile water of "suitable salinity" and packaged in sterile opaque containers wherein Cassidy et al. claim that the cells will remain viable for at least one year. According to Cassidy et al., the majority of the re-suspended cells packaged in this manner enter a metabolic state of inactivity (i.e. dormancy). The disclosure further states that the preserved cells can at any time be returned to their metabolically active state by adding ammonium chloride (or other suitable salt) to the opaque container to bring the ammonia concentration to about 200 ppm. There is also disclosed a method for rapid reactivation to complete metabolic activity within about 72 hours and subsequent addition into aquaria to begin oxidation and prevention of harmful ammonia accumulation in aquaria.

U.S. Pat. No. 5,733,774, issued to Jin et al., discloses stabilized bacteria that can survive long term storage at high temperatures. According to the method disclosed by Jin et al., bacteria are dried until they reach a dormant state. Suitable methods include air-drying, vacuum drying etc. See, Col. 2, lines 1–3. Next Oxygen is then removed from the environment surrounding the bacteria to prevent oxidative damage to the dormant cells. The bacteria is then packaged and stored in material impermeable to gas and water vapor, whereby Jin claims the bacteria will remain stable and efficacious for at least a year.

Several patents have been issued in reference to biochemical cycling and filtration methods. U.S. Pat. No. 3,957,634, issued to Orensten, et al., discloses a filtration means and method for aquarium systems in which water in the tank is purified in a biological/mechanical external filtration device. The biological portion of the filtering process contains nitrifying bacteria to assist in keeping the ammonia concentration in the aquarium system at a safe, nontoxic level.

U.S. Pat. No. 5,269,914, issued to Englert, discloses an undergravel filtration system for an aquarium that assists in the removal of toxic waste products in the tank by creating and maintaining colonies of aquatic anaerobic bacteria.

U.S. Pat. No. 5,679,253, issued to Fuerst, et al., discloses a rotating biological aquarium filter system that fosters the growth of aerobic bacteria on the surface of the filter body, reducing the level of toxins within the aquarium water.

U.S. Pat. No. 5,746,921, issued to Gargas, et al., discloses a fluidized bed aquarium filtration method for removing chemical and physical waste from an aquarium. The fluidized bed can include particles, such as sand, for removing ammonia from the water.

The methods disclosed by the background art fail to teach or suggest a method for rapid cycling an aquarium using bio-film attached to natural marine sand. Accordingly, there exists a need for a method of rapid cycling an aquarium using preserved ammonia-oxidizing bacteria available to consumers via retail sale and use in connection with salt-water aquaria. Furthermore, the background art fails to disclose a biochemical cycling method that includes granular substrate materials, such as aragonite reef sand, obtained directly from the ocean and containing the active biofilm required to present a true marine environment in an aquarium. Accordingly, there also exists a need for a method for introducing natural granular marine substrate material whereby rapid biochemical cycling occurs in connection with aquatic life in an aquarium.

BRIEF SUMMARY OF THE INVENTION

It is an object of the present invention to provide a method for preserving saltwater marine organisms for extended periods of time such that the organisms remain capable of metabolic and physiologic activity upon introduction into a marine aquarium during initial set-up.

One aspect of the invention relates to a method for rapid cycling of a marine aquarium using packaged marine substrate material, such as sand, aragonite, coral rock and crushed coral in an aqueous solution, suitable for retail display and sale, wherein a suitable environment is present so that marine microorganisms remain in biofilms attached to the surface of the material for extended periods of time. A further aspect of the invention relates to the discovery of a nutrient rich seawater enrichment solution containing vitamins, organics stock, trace metals, and $NaNO_3$ and $NaH_2PO_4H_2O$ for further extending the period of time wherein the organisms remain bioactive. Yet another aspect of the invention relates to a method for the introduction of naturally preserved granular marine substrate material containing live marine bacteria into an aquarium, wherein a suitable environment is present thereby enabling rapid biochemical cycling of organisms. Still another aspect of the invention relates to the survival of sensitive fish and invertebrates in captivity due to a naturally duplicated ecosystem and biochemical cycling process that maintains proper water chemistry necessary for aquatic life. The invention provides for the effective harvesting, packaging, transport, bio-active storage, and retail sale of aquarium substrate material containing live microorganisms, such as bacteria useful in oxidizing ammonia in aquariums, whereby the microorganisms remain biologically viable for extended periods of time in excess of twelve (12) months thereby maintaining a stable and healthy aquarium environment. The invention further provides for the effective and easy introduction of natural granular substrate material into an aquarium, thereby reducing harmful nitrates, maintaining proper pH, providing enhanced buffering capacity and essential inorganic elements which encourage a stable and healthy environment for aquatic life for extended periods of time.

Another object of the present invention is to provide a method for harvesting and packaging marine substrate material with an optimal amount of seawater and air in packaging specifically configured for maintaining ammonia-oxidizing bacteria in a state wherein the bacteria are capable of metabolic and physiologic activity after a prolonged period, at room temperature.

Still another object of the present invention is to provide an enrichment solution for prolonging the bio-active shelf life of marine microorganisms present in packaged marine substrate materials, such as aragonite, crushed coral, and sand.

Yet another object of the present invention is to provide a method for harvesting and packaging bio-actively optimal quantities of marine substrate material, air, seawater, and an enrichment solution for maintaining marine organisms in a biologically viable state for extended periods of time.

Still another object of the present invention is to provide packaging material that is specifically sized for prolonging the bio-active state of marine organisms when packaged in certain optimal quantities.

Yet another object of the present invention is to provide a method and composition for the preservation of microorganisms, associated with sand, shells, and coral materials harvested from natural marine environments, whereby the materials may be packaged in sealed containers, suitable for retail sale, within a unique enriched seawater solution.

Still another object of the present invention to provide a method for introducing naturally preserved granular marine substrate material containing active biofilm into a water-filled aquarium, whereby the biochemical cycling process is permitted to occur rapidly and effectively, further allowing nitrogenous waste to be properly removed while maintaining proper pH.

Yet another object of the present invention is to provide for the extended survival of sensitive fish and invertebrates in aquariums for indefinitely long periods of time due to a naturally duplicated ecosystem promoting the rapid biochemical cycling process that maintains the proper water chemistry necessary for aquatic life.

In accordance with these and other objects that will become apparent hereinafter, the instant invention will now be described with particular reference to the accompanying drawings.

BRIEF DESCRIPTION OF THE SEVERAL VIEWS OF THE DRAWINGS

FIG. 1 shows a formula for a seawater enrichment solution according to the present invention;

FIG. 2 shows the formula for the trace metal solution referenced in FIG. 1;

FIG. 3 shows the formula for the vitamin solution referenced in FIG. 1;

FIG. 4 shows the formula for the organics stock solution referenced in FIG. 1;

DETAILED DESCRIPTION OF THE INVENTION

Figure 5:
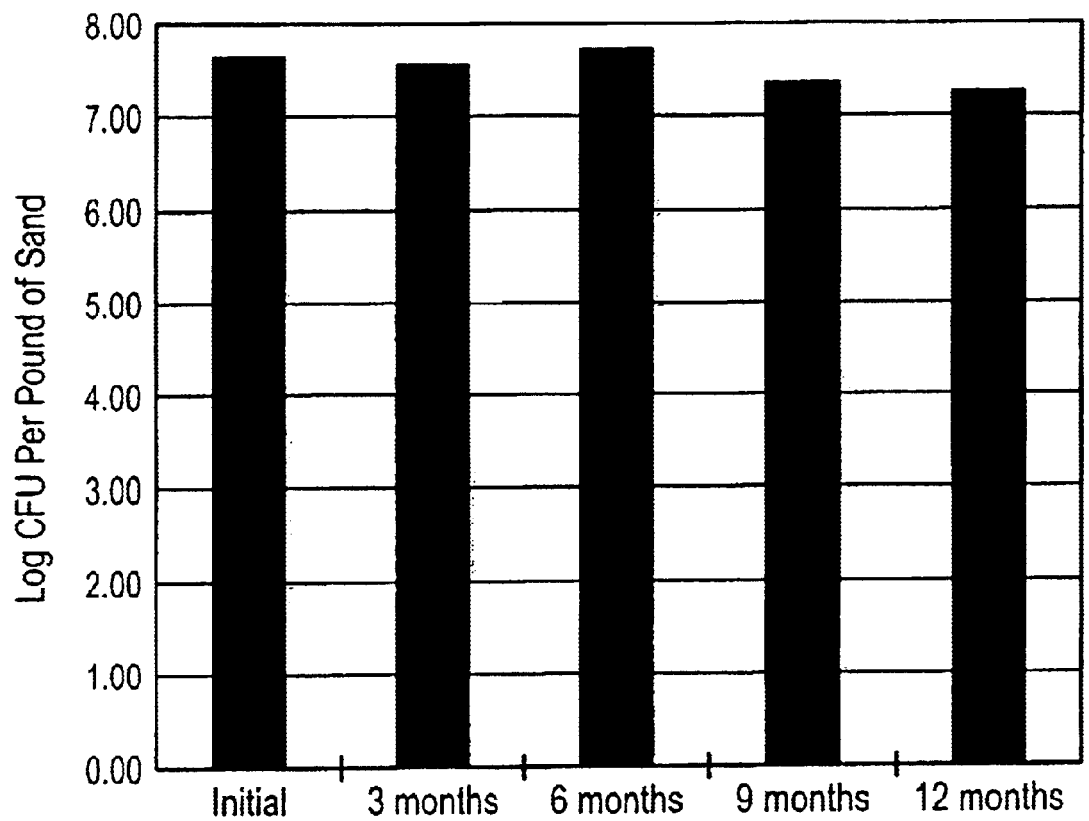
FIG. 5 is a graph depicting the number of colony forming units per pound ("CFU/Pound") of aragonite sand measured along the Y-axis and time in months measured along the X-axis as found on average in two different bags of aragonite packaged with an enrichment solution according to the present invention.

According to a first aspect of the present invention there is disclosed a method for rapid cycling an aquarium using preserved saltwater marine microorganisms, harvested from a natural marine environment, by introduction into an aquarium environment to facilitate rapid biochemical cycling. As used herein the term "marine microorganisms" and/or "microorganisms" shall mean aquatic bacteria naturally found in saltwater environments. Specifically, the method provides for the harvesting materials that are naturally rich with bacteria, such as sand, shells, aragonite, crushed coral materials, river rocks and pebbles and the like, harvested from submerged marine and/or river environments, and packaging the harvested materials in specifically sized sealed containers, suitable for storage at room temperature and retail sale, such that marine bacteria are preserved in their natural habitat—in biofilms attached to the granular surfaces—for extended periods of time. The method provides the aquarium industry with a useful means for prolonged storage of marine materials while maintaining microorganism bio-activity (i.e. metabolic and physiologic activity) such that, upon introduction into an aquarium environment the microorganisms are effective in biochemical cycling of the aquarium environment and stabilizing ammonia levels thereby resulting in an aquarium environment which is optimal for fish and other living organisms. According to a second aspect of the present invention there is disclosed an enrichment solution for further extending the period of time that the microorganisms remain bio-actively viable. The enrichment solution may be used in combination with the method of the first aspect of the invention to further enhance the period of time that microorganisms remain bio-actively viable. According to a third aspect of the present invention there is disclosed a method for introducing naturally preserved saltwater marine microorganisms into an aquarium environment to facilitate rapid biochemical cycling. According to a fourth aspect of the present invention there is disclosed a method providing for the extended survival of sensitive fish and invertebrates in aquariums due to a naturally duplicated ecosystem promoting the rapid biochemical cycling process thereby maintaining proper water chemistry necessary for aquatic life.

A first aspect of the present invention includes packaging marine substrate materials, such as aragonite, sand, crushed coral and the like according to the following steps:

1. Harvesting marine substrate material from a submerged marine environment;

2. Packaging the harvested marine material in said packaging along with saltwater and air in the following relative ratios: 1 lb. of sand with 2–12 fluid oz. (preferably between 4–6 fluid oz.) water and 5–100 $cm^3$ (preferably between 10–50 $cm^3$) of air.

3. Sealing the packages in an airtight manner.

It has been found that bacteria associated with marine material harvested and packaged in accordance with the above-referenced method steps is metabolically and physiologically active upon introduction into an aquarium environment. The process thus provides an optimal saltwater preservation solution and packaging method that results in the preservation of autotrophic marine bacteria in their natural habitat, i.e. a biofilm existing on the surfaces of the granular material. It is significant to the rapid cycling of aquarium tanks that the bacteria exist in biofilms as the bacteria in such a state are instantly capable of cycling harmful metabolic endproducts upon introduction into the aquarium environment. In contrast, the introduction of bacteria that has been cultured according to teachings of the background art, or bacteria that otherwise exists in a non-biofilm state, requires a substantial number of days and/or weeks to attach to aquarium materials and form biofilms prior to contributing to aquarium cycling.

Each pound of granular material harvested and packaged according to the present invention contains in excess of 10 million live bacteria. Each of the above-referenced steps contributes to a method of packaging harvested marine material whereby both autotrophic and heterotrophic bacteria survive in sealed packaging for longer periods of time than if packaged without one or more of the steps. According to the third aspect of the present invention, marine materials packaged according to the methods of the present invention are capable, upon introduction into an aquarium environment, of carrying out rapid biochemical cycling essential to the maintenance of a successful aquarium.

The first step provides for harvesting marine substrate material from a submerged marine environment and initially storing the harvested marine material in a sealed container with seawater. Harvesting the marine material, such as sand, from a submerged marine environment, as opposed harvesting dry material such as sand and crushed coral, is critical in obtaining material having an abundance of autotrophic and heterotrophic bacteria flourishing in established biofilm colonies. The material is typically initially stored within a container that may, or may not, be airtight, however, this step is one of practicality and is not deemed an important aspect of the present invention. The harvested sand includes some water such that it has the consistency of mud. Accordingly, any reference to the weight of the sand herein relates to the "wet" weight, e.g. the weight of mud as opposed to dry sand.

The second step requires providing packaging material having specific dimensional parameters such that marine material packaged therein preferably forms a uniform layer between ½-inch and 3-inches in depth. The 3-inch depth maximum limitation is considered important in that it allows both water and gas (contained in the packaging along with the harvested material as discussed below) to diffuse sufficiently through the material thereby providing vital, life-sustaining nutrients to the bacteria at all depths. It should be noted, however, that packaging the harvested material in layers exceeding the preferred 3-inch maximum is not a departure from the present invention as bacteria existing in the region of the top 3-inches of deeper layers will remain capable of metabolic and physiologic activity as described herein.

The third step includes depositing the harvested marine material in the packaging material along with seawater and air in the following relative ratios: 1 lb. of harvested material (e.g. sand, aragonite etc.); 2–12 fluid oz. (preferably between 4–6 fluid oz.) of seawater; and 5–100 $cm^3$ (preferably between 10–50 $cm^3$) of air. The fifth step includes sealing the packaging in an airtight manner.

It has been found that the above-referenced ratios of: (1) harvested material (forming a layer of 3-inches or less); (2) sea water; and (3) air; packaged in a sealed container provides a unique life sustaining environment wherein natural marine bacteria are capable of surviving for extended periods in excess of twelve (12) months. The retail packaging material preferably comprises a suitable plastic (either hard or soft/flexible). The contents of the package may be stored at room temperature without adversely affecting the biological viability of the marine bacteria. After an extended shelf life of twelve (12) months at room temperature, and after setting up the aquarium's filtering system and allowing it to circulate, in accordance with the third aspect of the present invention, the contents of the package may be introduced into the aquarium. This will allow rapid biochemical cycling to begin to remove nitrogenous waste and maintaining and/or restoring a natural organic balance thereby resulting in a healthy aquarium habitat. Further, in accordance with the fourth aspect of the present invention, the survival of sensitive fish and invertebrates in aquariums is extended due to a naturally duplicated ecosystem involving the rapid biochemical cycling process thereby maintaining proper water chemistry necessary for aquatic life.

According to a second aspect of the present invention there is disclosed an enrichment solution for further increasing the number of microorganisms that remain bio-actively viable. The enrichment solution may be used in combination with the method of the first aspect of the invention to further enhance the number of microorganisms that remain bio-actively viable during periods of extended storage. Specifically, a second aspect of the invention includes enriching the seawater used to package harvested marine material, such as sand, aragonite and crushed coral. According to the present invention an enrichment solution may include one or more of the following substances: a buffer; vitamins; proteins and/or amino acids; sugars; trace elements (e.g. minerals); Sodium Nitrate ($NaNO_3$); Sodium Phosphate ($NaH_2PO_4H_2O$).

In a preferred embodiment according to the second aspect of the present invention a sea water enrichment solution is prepared in accordance with the formula described in FIG. 1, whereby the solutions of FIGS. 2, 3, and 4 are combined with a predetermined quantity of sea water (filtered and sterilized after all additions), with predetermined quantities of Sodium Nitrate and Sodium Phosphate.

It has been found that the critical level of moisture necessary to keep the bacteria viable but dormant for more than six months is from 2 to 12 oz. of fortified, sterile-filtered, sea water per pound of live marine sand. Preferably 4 to 8 oz. of fortified sterile seawater is used. Most preferably, the critical level of moisture is generated by the addition of 6 oz. of fortified sterile-filtered seawater per pound of live marine material (e.g. sand, aragonite etc.). The seawater may be fortified with sterile seawater enrichment solution (FIG. 1; one liter of seawater enrichment solution is added to 100 gallons of seawater) and maintained in a sterile state until used.

It has been found that marine aragonite sand subjected to the process disclosed herein is likely to contain not less than 10,000,000 live heterotrophic bacteria per pound. The process results in a natural product that prevents bio-fouling, and contains live marine autotrophic bacteria to provide a proper inorganic balance. The beneficial characteristics of the process using aragonite sand include: (1) reducing harmful nitrate; (2) maintaining proper pH; (3) providing enhanced buffering capacity; and (4) providing essential inorganic elements such as strontium, cobalt, zinc, and molybdenum. In addition, the following trace elements are provided: Zinc Sulfate; Calcium Chloride, Manganese Chloride; Cobalt Chloride; Copper Sulfate; Sodium Molybdate; Strontium Chloride; Nickel Chloride; Potassium Bromide; and Sodium Silicate.

Attached hereto as Appendix A and B are Applicants' findings, over time, with respect to the amount of live bacteria per gram of marine aragonite reef sand packaged in accordance with the present invention both with the seawater enrichment solution (Appendix A) and without (Appendix B).

The instant invention has been shown and described herein in what is considered to be the most practical and preferred embodiment. It is recognized, however, that departures may be made therefrom within the scope of the invention and that obvious modifications will occur to a person skilled in the art.

APPENDIX A

VIABLE BACTERIAL COUNTS FOR BIO-ACTIV LIVE ™ ARAGONITE
(Preserved with Saltwater Enrichment Soultion)

| Media and Incubation Conditions | Dilution & Storage Conditions | Sample ID. | CFU/gm | Date Tested |
| --- | --- | --- | --- | --- |
| Marine Agar: At Room Temp | 1:10 - Kept at Room Temp | Bag #3 A | 83,941 | Apr. 26, 1998 |
| Marine Agar: At Room Temp | 1:10 - Kept at Room Temp | Bag #3 A | 86,622 | Apr. 26, 1998 |
| Marine Agar: At Room Temp | 1:10 - Kept at Room Temp | Bag #3 B | 101,199 | Apr. 26, 1998 |
| Marine Agar: At Room Temp | 1:10 - Kept at Room Temp | Bag #3 B | 99,425 | Apr. 26, 1998 |
| | | Average | 92,797 | |
| Marine Agar: At Room Temp | 1:10 - Kept at Room Temp | Bag #7 A | 78,877 | Jul. 19, 1998 |
| Marine Agar: At Room Temp | 1:10 - Kept at Room Temp | Bag #7 A | 86,594 | Jul. 19, 1998 |
| Marine Agar: At Room Temp | 1:10 - Kept at Room Temp | Bag #7 B | 86,093 | Jul. 19, 1998 |
| Marine Agar: At Room Temp | 1:10 - Kept at Room Temp | Bag #7 B | 76,556 | Jul. 19, 1998 |
| | | Average | 82,030 | |
| Marine Agar: At Room Temp | 1:10 - Kept at Room Temp | Bag #10 A | 121,619 | Oct. 5, 1998 |
| Marine Agar: At Room Temp | 1:10 - Kept at Room Temp | Bag #10 A | 125,307 | Oct. 5, 1998 |
| Marine Agar: At Room Temp | 1:10 - Kept at Room Temp | Bag #10 B | 99,334 | Oct. 5, 1998 |
| Marine Agar: At Room Temp | 1:10 - Kept at Room Temp | Bag #10 B | 99,966 | Oct. 5, 1998 |
| | | Average | 111,557 | |
| Marine Agar: At Room Temp | 1:10 - Kept at Room Temp | Bag #12 A | 83,941 | Jan. 5, 1999 |
| Marine Agar: At Room Temp | 1:10 - Kept at Room Temp | Bag #12 A | 38,905 | Jan. 5, 1999 |
| Marine Agar: At Room Temp | 1:10 - Kept at Room Temp | Bag #12 B | 44,173 | Jan. 5, 1999 |
| Marine Agar: At Room Temp | 1:10 - Kept at Room Temp | Bag #12 B | 45,440 | Jan. 5, 1999 |
| | | Average | 53,115 | |
| Marine Agar: At Room Temp | 1:10 - Kept at Room Temp | Bag #13 A | 37,756 | May 1, 1999 |
| Marine Agar: At Room Temp | 1:10 - Kept at Room Temp | Bag #13 A | 46,084 | May 1, 1999 |
| Marine Agar: At Room Temp | 1:10 - Kept at Room Temp | Bag #13 B | 50,780 | May 1, 1999 |
| Marine Agar: At Room Temp | 1:10 - Kept at Room Temp | Bag #13 B | 49,289 | May 1, 1999 |
| | | Average | 45,977 | |

APPENDIX B

VIABLE BACTERIAL COUNTS FOR BIO-ACTIV LIVE ™ ARAGONITE
(Without Saltwater Enrichment Soultion)

| Media and Incubation Conditions | Dilution & Storage Conditions | Sample ID. | CFU/gm | Date Tested |
| --- | --- | --- | --- | --- |
| Marine Agar: At Room Temp | 1:10 - Kept at Room Temp | Bag #2 A | 127,471 | Apr. 26, 1998 |
| Marine Agar: At Room Temp | 1:10 - Kept at Room Temp | Bag #2 A | 122,142 | Apr. 26, 1998 |
| Marine Agar: At Room Temp | 1:10 - Kept at Room Temp | Bag #4 B | 169,778 | Apr. 26, 1998 |
| Marine Agar: At Room Temp | 1:10 - Kept at Room Temp | Bag #4 B | 153,889 | Apr. 26, 1998 |
| | | Average | 143,320 | |
| Marine Agar: At Room Temp | 1:10 - Kept at Room Temp | Bag #5 A | 50,051 | Jun. 19, 1998 |
| Marine Agar: At Room Temp | 1:10 - Kept at Room Temp | Bag #5 A | 45,304 | Jun. 19, 1998 |
| Marine Agar: At Room Temp | 1:10 - Kept at Room Temp | Bag #8 B | 21,540 | Jun. 19, 1998 |

APPENDIX B-continued

VIABLE BACTERIAL COUNTS FOR BIO-ACTIV LIVE ™ ARAGONITE
(Without Saltwater Enrichment Soultion)

| Media and Incubation Conditions | Dilution & Storage Conditions | Sample ID. | CFU/gm | Date Tested |
| --- | --- | --- | --- | --- |
| Marine Agar: At Room Temp | 1:10 - Kept at Room Temp | Bag #8 B | 23,510 | Jun. 19, 1998 |
| | | Average | 35,101 | |
| Marine Agar: At Room Temp | 1:10 - Kept at Room Temp | Bag #11 A | 32,017 | Sep. 5, 1998 |
| Marine Agar: At Room Temp | 1:10 - Kept at Room Temp | Bag #11 A | 27,332 | Sep. 5, 1998 |
| Marine Agar: At Room Temp | 1:10 - Kept at Room Temp | Bag #11 B | 24,928 | Sep. 5, 1998 |
| Marine Agar: At Room Temp | 1:10 - Kept at Room Temp | Bag #11 B | 24,123 | Sep. 5, 1998 |
| | | Average | 27,100 | |
| Marine Agar: At Room Temp | 1:10 - Kept at Room Temp | Bag #12 A | 16,010 | Nov. 5, 1999 |
| Marine Agar: At Room Temp | 1:10 - Kept at Room Temp | Bag #12 A | 19,913 | Nov. 5, 1999 |
| Marine Agar: At Room Temp | 1:10 - Kept at Room Temp | Bag #12 B | 24,123 | Nov. 5, 1999 |
| Marine Agar: At Room Temp | 1:10 - Kept at Room Temp | Bag #12 B | 32,017 | Nov. 5, 1999 |
| | | Average | 23,016 | |
| Marine Agar: At Room Temp | 1:10 - Kept at Room Temp | Bag #1 A | 10,125 | Apr. 22, 1999 |
| Marine Agar: At Room Temp | 1:10 - Kept at Room Temp | Bag #1 A | 10,613 | Apr. 22, 1999 |
| Marine Agar: At Room Temp | 1:10 - Kept at Room Temp | Bag #1 B | 12,924 | Apr. 22, 1999 |
| Marine Agar: At Room Temp | 1:10 - Kept at Room Temp | Bag #1 B | 12,160 | Apr. 22, 1999 |
| | | Average | 11,456 | |

What is claimed is:

1. A method for rapid biochemical cycling of marine aquariums to establish a chemically balanced aquatic environment capable of supporting marine life, said method including the steps of:
   harvesting marine sand from a natural submerged marine environment, said sand containing marine microorganisms in the form of natural organic biofilm;
   depositing said sand in a container with a volume of seawater and a volume of air;
   said volume of seawater consisting of between 2 fluid ounces and 12 fluid ounces of seawater for every 1 pound of said sand; said volume of air consisting of between 5 cm$^3$ and 100 cm$^3$ for every 1 pound of said sand;
   sealing said container in an airtight manner, whereby said seawater and air provide a suitable environment for maintaining said marine microorganisms bio-actively viable;
   opening the sealed container and depositing the sand contained therein into a marine aquarium, whereby said marine microorganisms are effective in biochemical cycling of the aquarium environment and stabilizing ammonia levels thereby resulting in an aquarium environment which is suitable for supporting aquatic life.

2. A method for rapid biochemical cycling of a marine aquarium according to claim 1, wherein said volume of seawater is between 4 fluid ounces and 6 fluid ounces for every 1 pound of sand.

3. A method for rapid biochemical cycling of a marine aquarium according to claim 1, wherein said volume of air is between 10 cm$^3$ and 50 cm$^3$ for every 1 pound of sand.

4. A method for rapid biochemical cycling of a marine aquarium according to claim 1, wherein depositing said sand in a container includes distributing said sand in a generally uniform layer having a maximum depth of three inches.

5. A method for rapid biochemical cycling of a marine aquarium according to claim 1, further including the step of adding a microorganism enrichment solution to said container.

6. A method for rapid biochemical cycling of a marine aquarium according to claim 5, wherein said enrichment solution includes a pH buffer.

7. A method for rapid biochemical cycling of a marine aquarium according to claim 5, wherein said enrichment solution includes vitamins.

8. A method for rapid biochemical cycling of a marine aquarium according to claim 5, wherein said enrichment solution includes proteins.

9. A method for rapid biochemical cycling of a marine aquarium according to claim 5, wherein said enrichment solution includes amino acid.

10. A method for rapid biochemical cycling of a marine aquarium according to claim 5, wherein said enrichment solution includes sugar.

11. A method for rapid biochemical cycling of a marine aquarium according to claim 5, wherein said enrichment solution includes trace elements.

12. A method for rapid biochemical cycling of a marine aquarium according to claim 5, wherein said enrichment solution includes $NaNO_3$.

13. A method for rapid biochemical cycling of a marine aquarium according to claim 5, wherein said enrichment solution includes $NaH_2PO_4H_2O$.

14. A method for rapid biochemical cycling of a marine aquarium according to claim 5, wherein said enrichment solution includes Sodium Phosphate.

15. A method for rapid biochemical cycling of marine aquariums to establish a chemically balanced aquatic environment capable of supporting marine life, said method including the steps of:
   harvesting marine sand from a natural submerged marine environment, said sand containing marine microorganisms in the form of natural organic biofilm;
   depositing said sand in a container with a volume of seawater and a volume of air, such that said sand forms a generally uniform layer having a maximum depth of three inches;
   said volume of seawater consisting of between 2 fluid ounces and 12 fluid ounces of seawater for every 1 pound of said sand;
   said volume of air consisting of between 5 cm$^3$ and 100 cm$^3$ for every 1 pound of said sand;
   sealing said container in an airtight manner, whereby said seawater and air provide a suitable environment for maintaining said marine microorganisms bio-actively viable;
   opening the sealed container and depositing the sand contained therein into a marine aquarium, whereby said marine microorganisms are effective in biochemical cycling of the aquarium environment and stabilizing ammonia levels thereby resulting in an aquarium environment which is suitable for supporting aquatic life.

* * * * *